(12) United States Patent
Hofeldt (10) Patent No.: US 7,290,878 B1
(45) Date of Patent: Nov. 6, 2007

(54) MACHINE FOR BINOCULAR TESTING AND A PROCESS OF FORMATTING RIVAL AND NON-RIVAL STIMULI

(76) Inventor: Albert John Hofeldt, 314 W. San Marino Dr., Miami Beach, FL (US) 33139

( * ) Notice: Subject to any disclaimer, the term of this patent is extended or adjusted under 35 U.S.C. 154(b) by 739 days.

(21) Appl. No.: 10/686,272

(22) Filed: Oct. 15, 2003

(51) Int. Cl.
*A61B 3/08* (2006.01)

(52) U.S. Cl. ...................................... 351/201; 351/200

(58) Field of Classification Search ................ 351/200, 351/201, 204, 246
See application file for complete search history.

(56) References Cited

U.S. PATENT DOCUMENTS 4,863,258 A * 9/1989 Greene ....................... 351/201
5,764,340 A * 6/1998 Hofeldt ....................... 351/201
6,851,807 B2 * 2/2005 Holdeman ................... 351/203

* cited by examiner

*Primary Examiner*—Huy Mai (57) ABSTRACT

A process for formatting rivalrous fusible images having similarly shaped stimuli of similar binocular luminance and having other similarly shaped stimuli of different binocular luminance, which metamorphose during perception into identifiable shapes that distinguish fusion from suppression. The preferred embodiment is an invertible stereoscope for viewing rivalrous images, non-rivalrous images, and stereograms, having adjustable eyepieces, lighting control of front and rear chambers, and lighting control of right and left sides. In a further preferred embodiment, rivalrous stimuli in a complementary color scheme are viewed on printed material or on a computer screen through lenses of complementary colors. Neutral density filter placement that asymmetrically attenuates light to the eyes for detection of subthreshold afferent defects is disclosed.

13 Claims, 10 Drawing Sheets

MACHINE FOR BINOCULAR TESTING AND A PROCESS OF FORMATTING RIVAL AND NON-RIVAL STIMULI

CROSS REFERENCE TO RELATED APPLICATIONS

Not Applicable

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of binocular vision testing and more specifically to a process for detecting disease by viewing rival contour elements.

During natural viewing, the two eyes send similar information to the brain concerning the images in the visual space. Images of different colors that occupy the same visual space can only be presented to the eyes by using artificial means such as a stereoscope, polarized images viewed through polarizing glasses, or complementary colored images viewed through lenses of complementary colors. When dissimilar but fusible images occupy the same visual space, rivalry ensues and the two dissimilar images compete for recognition. The two images may fuse to form a composite image or one rival image will be suppressed while the other image is seen. Images of different shapes will not fuse when their shapes differ too greatly.

Binocular rivalry has the potential usefulness of identifying conditions affecting the visual system, particularly if opposing rival endpoints are easily identifiable. Normally, nerve impulses traveling along the two optic nerves travel at the same velocity. When a disease affects neural transmission, the impulses from the defective eye travel at a slower velocity than the impulses from the healthy eye. When nerve impulses from one eye are conducted at a slower velocity than impulses from the opposite eye, a relative (one eye compared to the other eye) afferent (towards the brain or sensory) defect occurs. Due to slowing of the nerve conduction by the disease process, the nerve impulses on the side of the afferent defect will be delayed reaching the brain. The brain perceives the earlier arriving impulses (data of one rival component) from the healthy eye and suppresses the later arriving impulses (data of the opposing rival component) from the defective eye. A relative afferent defect can result from injury or disease of the eye, optic nerve, or brain. In amblyopia, the dysfunction responsible for the relative afferent defect is thought to be a dysfunction in processing of information by the brain.

Dimming the light to one of the two eyes can simulate a relative afferent defect. Similar to a disease process, dimming the light delays the nerve impulses traveling from that eye compared to the opposite brighter illuminated eye. Conversely, a simulated relative afferent defect can be measured by reducing the light to the brighter illuminated eye until the relative afferent defect is reversed. When disease affects one eye more than the other eye, the relative afferent defect can be counterbalanced and measured by dimming the light on the side of the healthy eye. This slows the nerve impulses originating from the healthy eye and allowing impulses from the defective (suppressed) eye to reach the brain first and be perceived.

Rivalry of black and white identically shaped images has been shown to produce a lustrous "gun metal" phenomenon by H. von Helmholtz (Handbuch der Physiologischen Optik, 1910). Greene (U.S. Pat. No. 4,863,258) demonstrated that by framing one image of an image pair of differing colors with a black border along two contiguous sides of the image or by circling the image with a black ring or border, the binocular perception would be a bright lustrous image. According to Greene, the perception of the dark border controls and determines the synthesis of information from the two eyes, and causes the stimulus material lying inside the boundary to dominate perception. Greene's invention is limited to the production of rival conditions by means of a dark border to produce the visual perception of luster. Hofeldt (U.S. Pat. No. 5,764,340) demonstrated that by using different colors as rival images without regard to borders, rivalry of colors could be used to measures visual function with the endpoint being the perception of one color over the complementary color without regard to the perception of luster.

Current techniques for distinguishing suppression from fusion of rival images require the subject to recognize the presence of luster (Greene) or identify different colors (Hofeldt). Both these endpoints are difficult concepts for children and some adults to comprehend. Luster is a subtle unnatural and dazzling phenomenon which requires education before it can be recognized. A rival test with easily identifiable images that distinguishes fusion from suppression would improve the usefulness of rivalry testing.

Current stereoscopes, for example the View-Master®, have a fixed interpupillary distance that fit either adults or children, but not both. These stereoscopes have one illuminated chamber and the illumination of the image pair is equal and uniform. There is no means for presenting scenes having areas differing in brightness. For example, in the modified View-Master® described by Hofeldt (U.S. Pat. No. 5,764,340), the reel contains neutral density filters and when engaged the entire scene dims which includes rival, binocularity, and stereoscopic stimuli. This global dimming on one side is an obvious clue to the subject of which eye is being suppressed.

Current stereoscopes are not used for viewing in both the upright and the inverted positions. Images for these stereoscopes are legible in only the upright position.

BRIEF SUMMARY OF THE INVENTION

The primary object of the invention is to provide rival fusible images that metamorphose during perception to identifiable shapes distinguishing fusion from suppression, which makes the endpoint easier to identify than previous methods of color discrimination and recognition of luster.

Another object of the invention is to provide a stereoscope with adjustable eyepieces that accommodates different interpupillary distances of children and adults.

Another object of the invention is to provide a stereoscope that combines rivalry, fusion, and stereopsis testing.

Another object of the invention is to provide an invertible stereoscope that can be viewed in the upright or inverted position.

Another object of the invention in to provide a stereoscope with two separately illuminated chambers so that a scene can have areas of different brightness.

Another object of the invention is to provide stimulus lighting that is controlled by a flasher and a timer.

Another object of the invention is to provide a stereoscope with adjustable lighting on the right and left sides.

Another object of the invention is to provide a rivalry test applicable to children or adults.

Another object of the invention is to provide a test that is simple to understand and requires no new skills of the subject.

Another object of the invention is to provide a protocol for a rival vision test that separates normal from abnormal responses and identifies which eye is abnormal.

Another object of the invention is to provide a method to quantify the loss in vision.

Another object of the invention is to provide a rival vision test that can be displayed in a stereoscope.

Yet another object of the invention is to provide a rival vision test than can be displayed on printed material.

A further object of the invention is provide a rival vision test that can be displayed on a computer monitor and transmitted on the Internet.

Yet a further object of the invention is to provide a method for selective attenuation of light to one eye in order to amplify a relative afferent defect and elevate a small defect to a detectable level.

Other objects and advantages of the present invention will become apparent from the following descriptions, taken in connection with the accompanying drawings, wherein, by way of illustration and example, embodiments of the present invention are disclosed.

A stereoscope capable of housing a variety of tests and a process for formatting rival images that combine non-rival and rival contours for detection of disease is disclosed. Each monocular rival image is different and fusible to form a binocular image distinct from one or both monocular images. The invention has three modes of presenting rival images; with a stereoscope, on printed material, and by computer processing. The stereoscope has a two-way mirror creating two chambers with separate lighting that allows simultaneous viewing of two parts of the scene at different brightness levels. The brightness difference between the right and left sides is also adjustable. Glasses with complementary lenses are used for image separation when rival stimuli are presented on printed material or by computer processing. A lens arrangement for binocular asymmetrically brightness is disclosed, which amplifies a small relative afferent defect to a level detectable by rivalry testing.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

REFERENCE NUMERALS IN DRAWINGS

| | Reference Numerals in Drawings |
|---|---|
| 1. | Stereoscope |
| 2A. | Adjustable eyepiece, right |
| 2B. | Adjustable eyepiece, left |
| 3A. | Optical lens, right |
| 3B. | Optical lens, left |
| 4A. | Lever for optical lens 3A |
| 4B. | Lever for optical lens 3B |
| 5. | Lever for film carriage |
| 6A. | Lever for 0.9 log units neutral density filter |
| 6B. | Lever for 0.6 log unit neutral density filter |
| 6C. | Lever for 0.3 log unit neutral density filter |
| 7A. | Support brace for eyepiece 2A |
| 7B. | Support brace for eyepiece 2B |
| 8A. | Light for front chamber, right |
| 8B. | Light for front chamber, left |
| 9. | Front chamber |
| 10. | Backdrop panel |
| 11. | Two way mirror |
| 12. | Film carriage |
| 13A. | Neutral density filter carriage |
| 13B. | Neutral density filter carriage |
| 13C. | Neutral density filter carriage |
| 14A. | Partition |
| 14B. | Partition |
| 14C. | Partition |
| 15. | Opaque diffuser |
| 16. | Support bar |
| 17. | Contact bar |
| 18A. | Bolt connecting 16 to 17 |
| 18B. | Bolt connecting 16 to 17 |
| 19. | Rear chamber |
| 20. | Battery |
| 21A. | Rear chamber light, right |
| 21B. | Rear chamber light, left |
| 22A. | Mount for light 21A |
| 22B. | Mount for light 21B |
| 23. | Flasher |
| 24. | Timer |
| 25A. | Switch for front chamber |
| 25B. | Switch for rear chamber |
| 26A. | Corner support |
| 26B. | Corner support |
| 26C. | Corner support |
| 26D. | Corner support |
| 27A. | Side panel, right |
| 27B. | Side panel, left |
| 28A. | Front panel, right |
| 28B. | Front panel, left |
| 29. | Rear panel |
| 30. | Pathway of light |
| 31. | Transparent film |
| 32. | Compression spring |
| 33A. | Plunger |
| 33B. | Plunger |
| 33C. | Plunger |
| 33D. | Plunger |
| 40A. | Optical opening, right |
| 40B. | Optical opening, left |

-continued

| | Reference Numerals in Drawings |
|---|---|
| 41A. | Indentation stop for plunger |
| 41B. | Indentation stop for plunger |
| 41C. | Indentation stop for plunger |
| 41D. | Indentation stop for plunger |
| 41E. | Indentation stop for plunger |
| 41F. | Indentation stop for plunger |
| 42A. | Optical opening, right |
| 42B. | Optical opening left |
| 43A. | "Block" stereo target, right |
| 43B. | "Block" stereo target, left |
| 44A. | "Moon" stereo target, right |
| 44B. | "Moon" stereo target, left |
| 45A. | "Sun" stereo target, right |
| 45B. | "Sun" stereo target, left |
| 46. | Non-fusional target, left |
| 47. | Non-fusional target, right |
| 51A. | Neutral density filter, right |
| 51B. | Neutral density filter, left |
| 52A. | Hole for plunger, right |
| 52B. | Hole for plunger, left |
| 53A. | Rival image, digit 6 |
| 53B. | Rival image, digit 9 |
| 54A. | Rival image, digit 5 |
| 54B. | Rival image, digit 2 |
| 55A. | Hole for plunger, right |
| 55B. | Hole for plunger, left |
| 56. | Ledge for film, superior |
| 57. | Ledge for film, inferior |
| 64. | Black line segment rival to 65 |
| 65. | White line segment rival to 64 |
| 66. | Black line segment rival to 67 |
| 67. | White line segment rival to 66 |
| 68. | Black line segment rival to 69 |
| 69. | White line segment rival to 68 |
| 70. | Black line segment rival to 71 |
| 71. | White line segment rival to 70 |
| 72. | Percept, digit 8 |
| 73. | Percept, digit 2 |
| 74. | Percept, digit 5 |
| 75. | Percept, digit 8 |
| 76. | Percept, digit 5 |
| 77. | Percept, digit 2 |
| 80. | Stimulus |
| 81. | Black line segment |
| 82. | Red line segment |
| 83. | Blue line segment |
| 84. | Pale red line |
| 85. | Pale blue background |
| 86A. | Glasses with red lens on right |
| 86B. | Glasses with red lens on left |
| 87. | Blue tinted lens |
| 88. | Red tinted lens |
| 89. | Percept, digit 6 |
| 90. | Percept, digit 9 |
| 91. | Composite image seen through blue lens, digit 9 |
| 92. | Composite image seen through red lens, digit 6 |
| 93. | Percept, digit 8 |
| 100A. | Composite stimulus, digit 8, 1st in series |
| 100B. | Composite stimulus, digit 8, 3rd in series |
| 100C. | Composite stimulus, digit 8, 5th in series |
| 101A. | Composite stimulus, digit 0, 2nd in series |
| 101B. | Composite stimulus, digit 0, 4th in series |
| 101C. | Composite stimulus, digit 0, 6th in series |
| 102. | Lines, white color |
| 103. | Background, gray color |
| 104. | Fusible red stimulus, digit 8 |
| 106. | Percept, digit 0 |
| 107. | Fusible blue stimulus, digit 0 |
| 108. | Composite image seen through blue lens, digit 8 |
| 109. | Composite image seen through red lens, digit 0 |
| 110. | Black line segment rival to 111 |
| 111. | White line segment rival to 110 |
| 112. | Position on the monitor |
| 120. | "Face" stimulus |
| 121. | Lines, gray color |
| 122. | "Happy face" contour, pale blue |
| 123. | "Sad face" contour, pale red |

-continued

| | Reference Numerals in Drawings |
|---|---|
| 124. | Composite image seen through blue lens, "sad face" |
| 125. | Composite image seen through red lens, "Happy face" |
| 128. | "Talking face" |
| 129. | Percept, "sad face" |
| 130. | Percept, "happy face" |
| 140. | Neutral density filter |
| 141. | Complementary colored glasses with neutral density filter attached |

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

Figure 1:
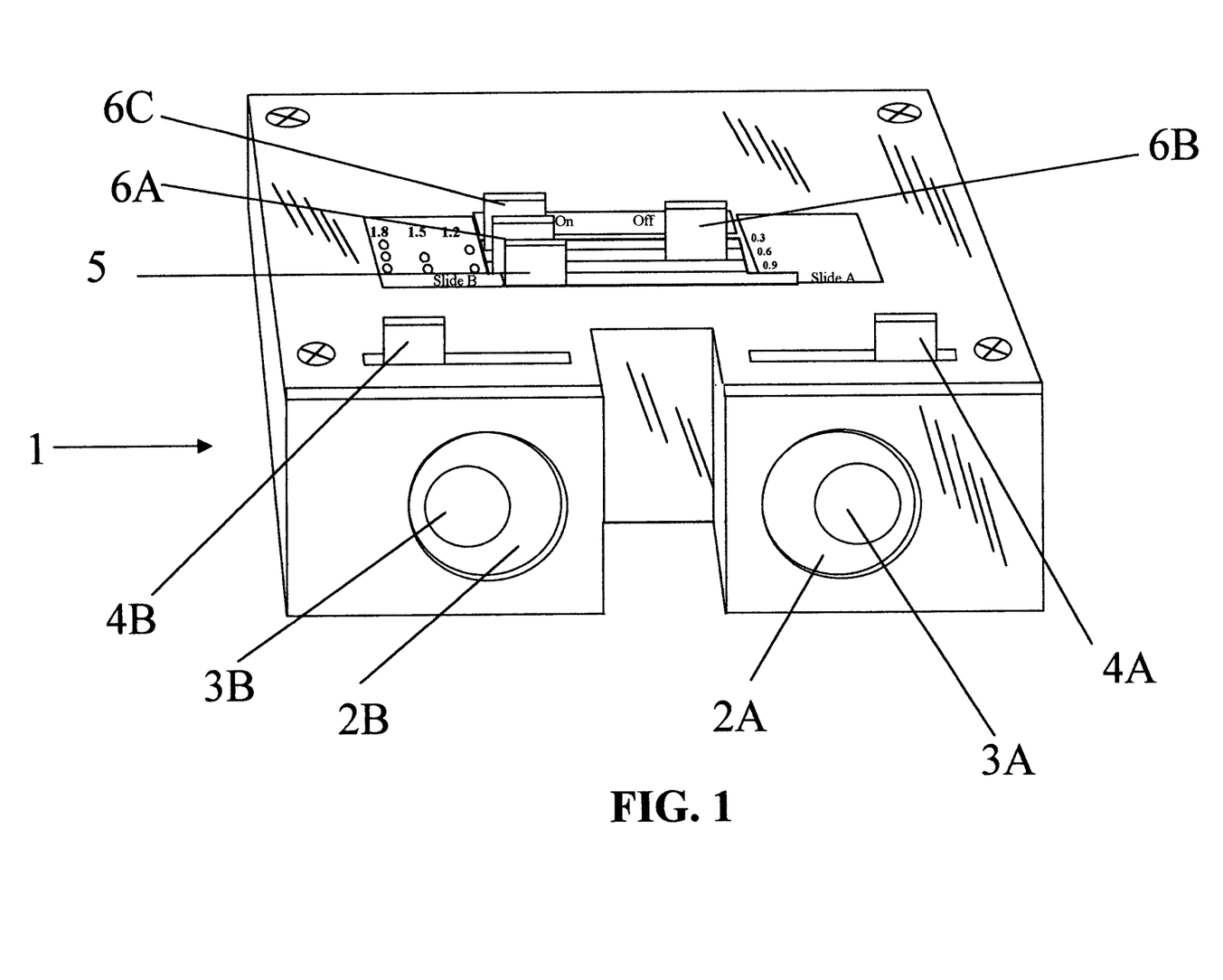
FIG. 1 is a perspective view of the stereoscope.

The preferred embodiment is hand-held stereoscope 1 illustrated in FIG. 1. Stereoscope 1 has adjustable eyepieces 2A and 2B that hold optical lenses 3A and 3B that move medially and laterally by sliding lever 4A and 4B. On the top of stereoscope 1 is lever 5 of carriage 12 (FIG. 2) that moves left and right to change the alignment of the rival stimuli seen through eyepieces 2A and 2B. To control the brightness difference between the two sides of rear chamber 19 (FIG. 2), levers 6A, 6B, and 6C are moved to the left or right to selectively attenuate the illumination to one eye, however, an alternative method of dimming is by controlling each light with a rheostat. In the preferred embodiment neutral density filters of 0.3, 0.6 and 0.9 log units are illustrated, however, other values can be used. The neutral density filters can be engaged singularly or combined for additive light attenuation.

Figure 2:
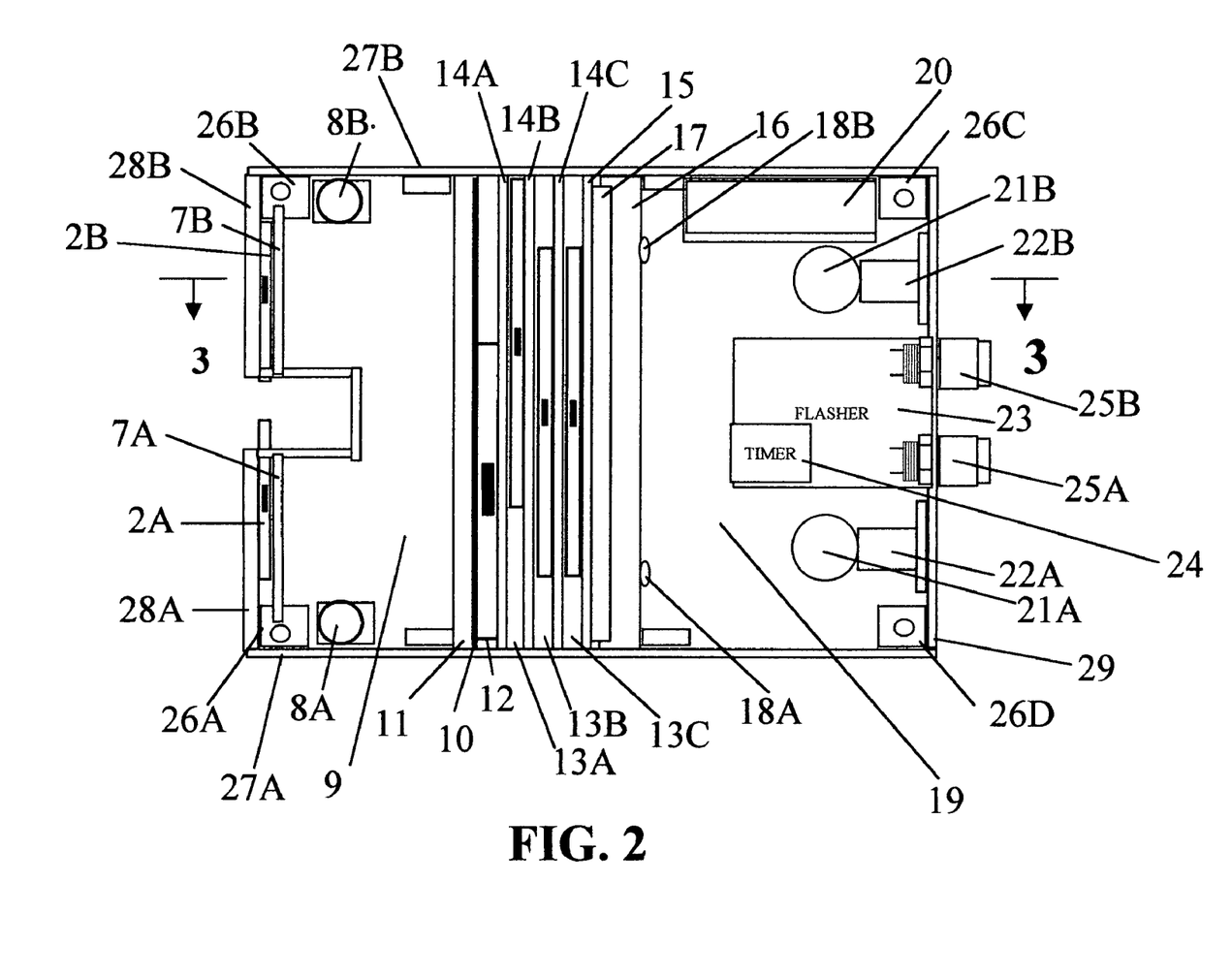
FIG. 2 is a plan view of the stereoscope.

In FIG. 2 braces 7A and 7B support eyepieces 2A and 2B. Switch 25A activates lights 8A and 8B in front chamber 9 that illuminates backdrop panel 10 through two-way mirror 11. Carriages 13A, 13B, and 13C house the neutral density filters. Sandwiched between the carriages are partition panels 14A, 14B, and 14C that have opening for unobstructed light transmittance. Panel 15 is an opaque diffuser. Support bar 16 holds contact bar 17. Bars 16 and 17 are connected by bolts 18A and 18B. Rear chamber 19 contains battery 20, electric light bulbs 21A and 21B, light bulb mounts 22A and 22B, and adjustable flasher 23 and adjustable timer 24 for lights 21A and 21B. Flasher 23 controls the off and on rate of lights 21A and 21B, and timer 24 controls the period that light bulbs 21A and 21B are activated. Switch 25B activates flasher 23, timer 24, and bulbs 21A and 21B. Corner supports 26A, 26B, 26C, and 26D support side panels 27A and 27B, front panels 28A and 28B, and rear panel 29.

Figure 3:
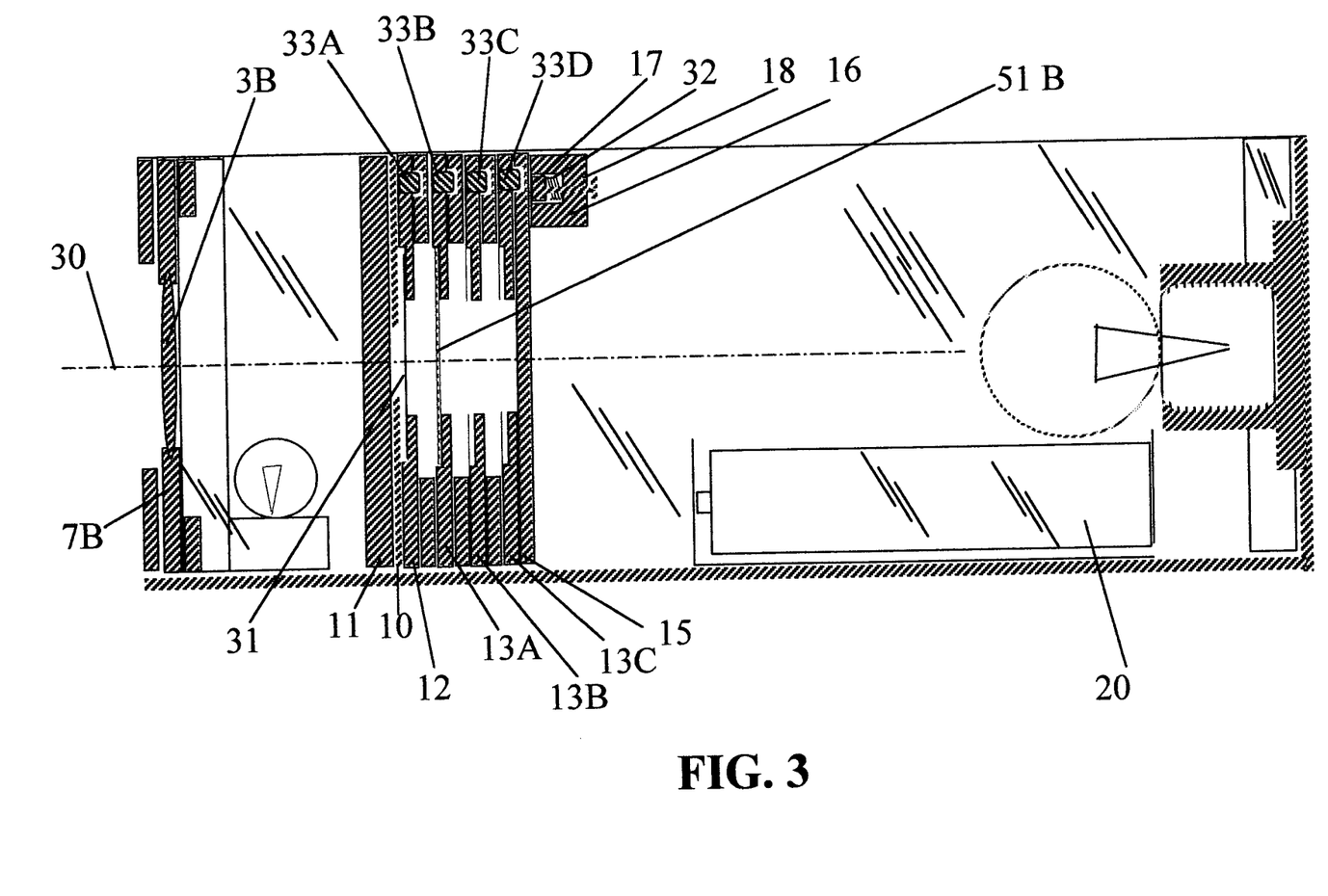
FIG. 3 is a cross sectional view of the stereoscope.

FIG. 3 is cross-section 3 of FIG. 2 and shows pathway of light 30 passing through opaque diffuser 15, neutral density filter 51B, transparent film 31, two-way mirror 11, and lens 3B. Plungers 33A-D screw into carriages 12 and 13A-C, and seat into indentations in panels 14A-C and 15. Support bar 16 holds contact bar 17 against panel 15 and the force generated by compression spring 32 is transferred to all elements between panel 15 and two-way mirror 11. The tension of compression spring 32 is such that the plungers stop the carriage at designated positions and yet the carriage slides easily.

Figure 4A:
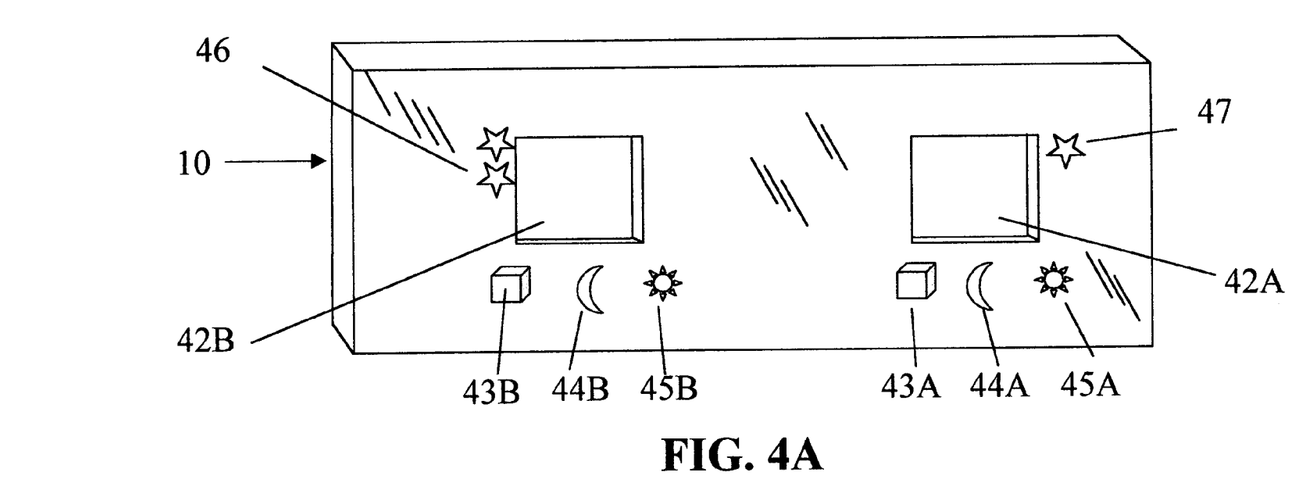
FIG. 4A is a perspective view of the backdrop panel 10 of the stereoscope.
Figure 4B:
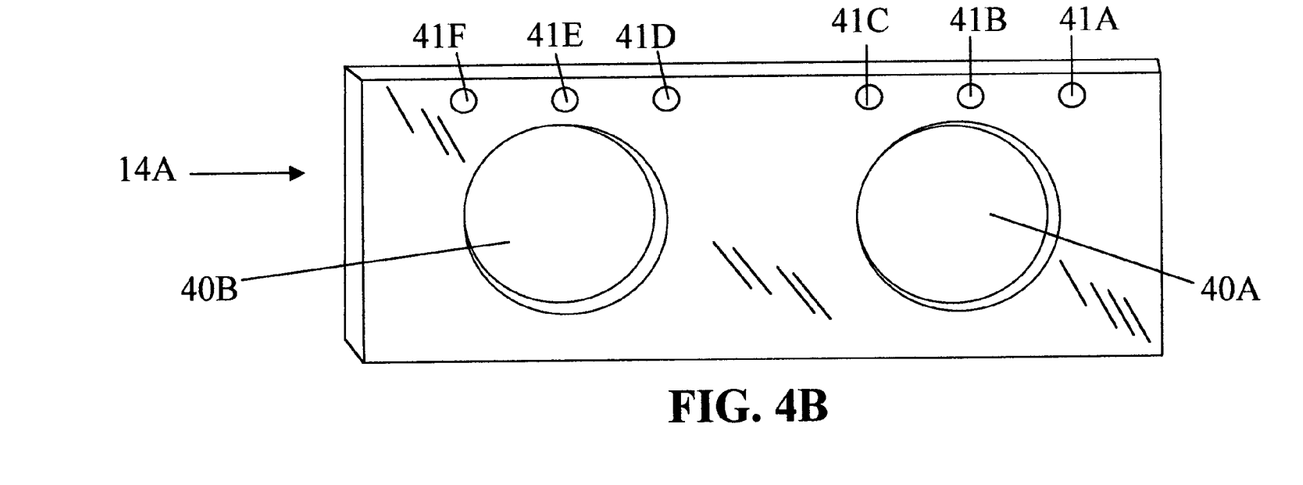
FIG. 4B is a perspective view of partition panel 14A of the stereoscope.

In FIG. 4A is backdrop panel 10 with optical openings 42A and 42B, stereogram targets 43A and 43B, 44A and 44B, and 45A and 45B, and non-fusional targets 46 and 47. In FIG. 4B is illustrated panel 14A showing optical openings 40A and 40B and indentations 41A-F are stops for the plungers.

Figure 5A:
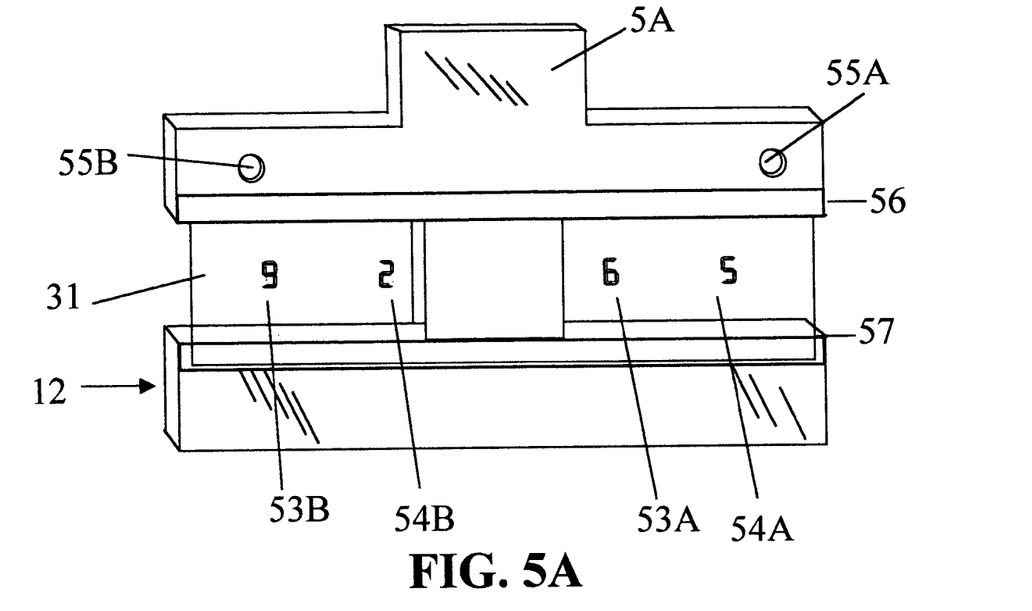
FIG. 5A is a perspective view of film carriage 12.
Figure 5B:
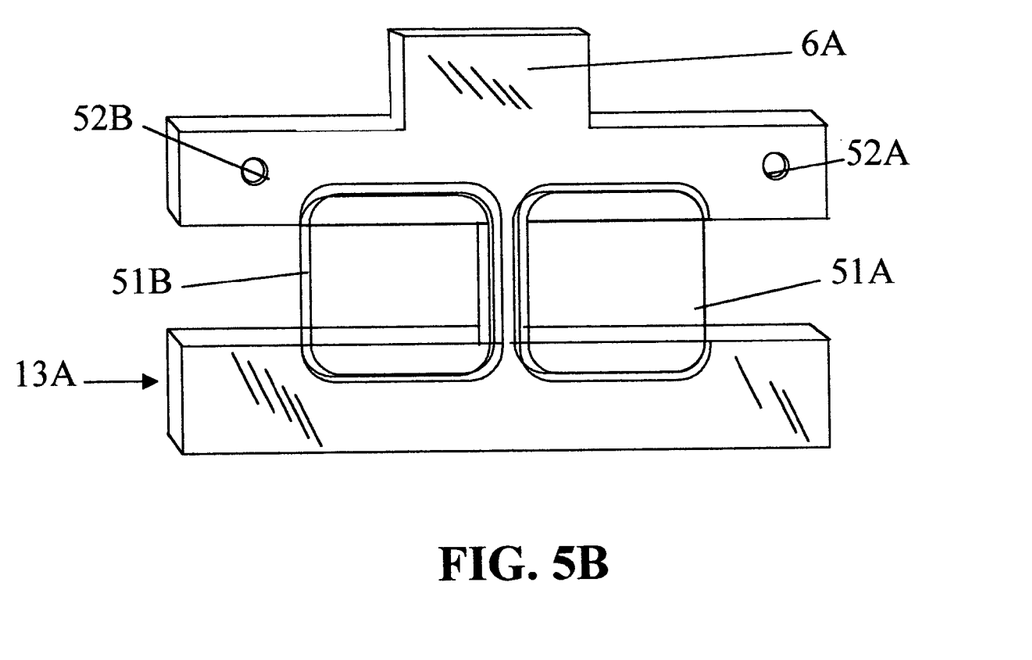
FIG. 5B is a perspective view of the carriage 13A holding neutral density filters.

In FIG. 5A carriage 12 has superior ledge 56 and inferior ledge 57 to hold transparent film 31 having paired rival images 53A and 53B, and 54A and 54B. Threaded holes 55A and 55B house threaded plungers. In FIG. 5B is carriage 13A with lever 6A, neutral density filter 51A and 51B, and threaded holes 52A and 52B that house plungers.

Figure 6A:
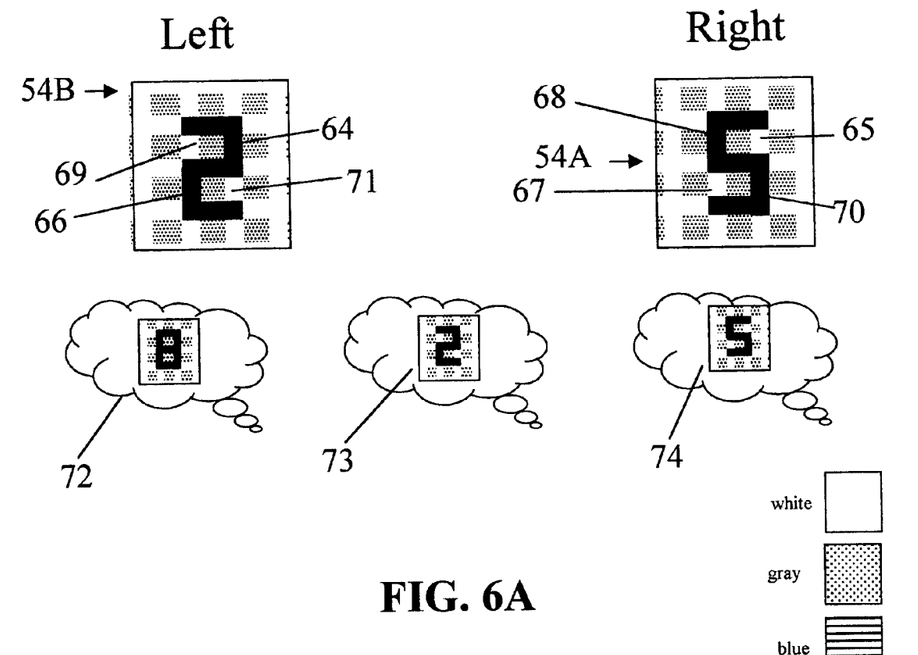
FIG. 6A is a schematic diagram illustrating rival images and percepts of the images in the upright position.

In FIG. 6A are rival image pair 54A and 54B of stereoscope 1 that are made up of identically shaped segments with some paired segments of the same luminance and other paired segments of different luminance. Because of the difference in luminance of paired segments in image pair 54A and 54B, distinctive images are visible, namely the digit 5 and the digit 2. Item 54A consists of white lines, a gray background, and five black line segments forming the digit 5. Image 54B consists of white lines and a gray background, and five black line segments forming the digit 2. Images 54A and 54B have four paired rival stimuli: black line segment 64 rivals with white line segment 65, black line segment 66 rivals with white line segment 67, black line segment 68 rivals with white line segment 69, and black line segment 70 rivals with white line segment 71. FIG. 6A is the appearance of image pair 54A and 54B when stereoscope 1 is in the upright position. With stereoscope 1 upright, fusion of the image 54A and 54B results is percept 72, the digit 8. Suppression of the right eye gives percept 73 or the digit 2, and suppression of the left eye gives percept 74 or the digit 5.

Figure 6B:
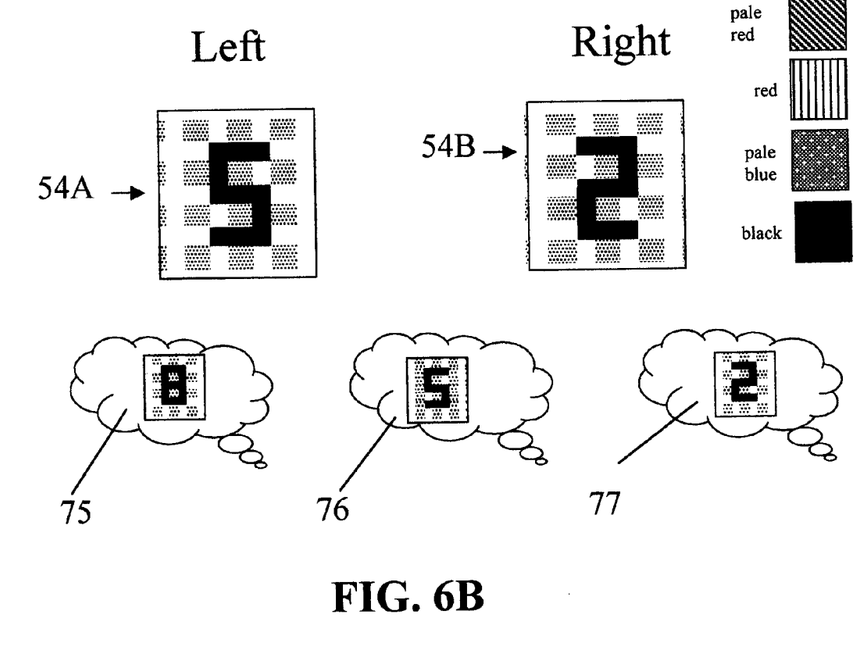
FIG. 6B is a schematic diagram illustrating rival images and percepts of the images in the upside-down position.

In FIG. 6B stereoscope 1 is inverted as compared to 6A. The digits for the images chosen are digits that are legible when upright or inverted. Inverting the stereoscope has the benefit of comparing the two eyes under the identical interocular lighting difference while viewing different images. When the illumination is dimmer to one eye, inverting stereoscope 1 reverses the eye viewing the dimmer image without changing the interocular brightness difference. With the stereoscope inverted, fusion of the image 54A and 54B results is percept 75, the digit 8. Suppression of the right eye gives percept 76 or the digit 5, and suppression of the left eye gives percept 77 or the digit 2. The digits 2 and 5 are only examples of rival images, any contour image pair can be used that have contour elements in common. In the preferred embodiment rival stimulus pairs are black and white, however, any color combination can be used that differ in luminance.

Figure 7:
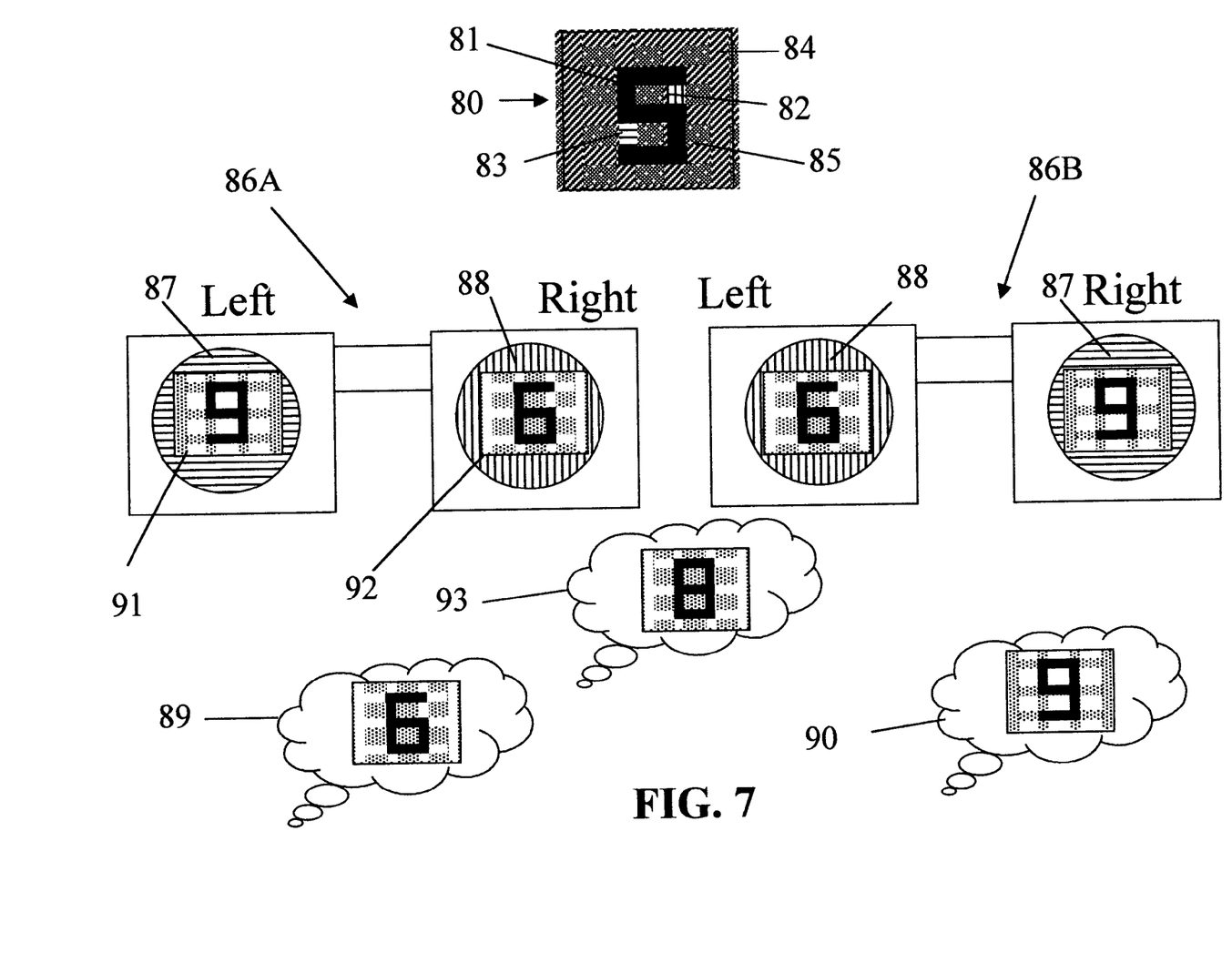
FIG. 7 is a schematic diagram illustrating an image with rival contours of complementary colors.

In FIG. 7 is another embodiment of my invention where the image is printed on material and viewed through tinted lenses. A single image or a series is compiled for viewing through lenses of red and blue complementary colors. A tinted lens transmits light of the same color and blocks light of all other (complementary) colors, that is, complementary colors are blocked from transmittance through the lens. When a tinted lens completely transmits a color, the item of that color will appear colorless or invisible. When a tinted lens completely blocks the transmittance of a color, an item of that color appears black. When a lens incompletely transmits a color, the item of that color appears less luminous and is perceived as a shade of gray. An example of a stimulus of this embodiment begins with five segments of black line segment 81, to form a recognizable symbol; in this example, the digit 5 in stimulus 80. Other elements, such as, red line segment 82 and blue line segment 83 are added and when viewed through red lens 88 and blue lens 87 transform the digit 5 to two distinctive different symbols that are also readily identifiable, namely digits 6 and 9. Glasses having complementary tinted lenses can be in position 86A with the red lens 88 over the right eye and the blue lens 87 over the left eye or in position 86B with the red lens 88 over the left eye and the blue lens 87 over the right eye. The right and left labels signify visual orientation. Red lens 88 blocks both black 81 (digit 5) and blue line segment 83 forming the composite image 92 (digit 6). Blue lens 87 blocks both black lines of segment 81 (digit 5) and red line segment 82 forming composite image 91 (digit 9). When differently shaped rival images 91 (digit 6) and 92 (digit 9) fuse, the perception is percept 93 (digit 8) that is distinctly different than rival images 91 and 92.

Look again at FIG. 7. Line 84 is pale red and is one of the vertical and horizontal lines of the same color that mimic the direction and width of the line segments forming the digit 8. Background 85 is pale blue and is located between the vertical and horizontal lines. In parallel with one lens color and complementary to the other lens color of lenses 87 and 88, the red and blue pale colors (the line 84 and background 85) intensify the contrast during suppression and make the digit stand out prominently. During fusion as in percept 93 (digit 8), the lines and the background fluctuate between white and gray. In contrast, during suppression the background is gray and the lines are white as in percept 89 or the background is white and the lines are gray as in percept 90, depending upon which side is suppressed.

A further embodiment of my invention is visual stimuli presented by a computer program and displayed on a monitor or projection on a screen, or transmitted over the Internet. For binocular image separation, images follow a complementary color scheme and viewing is through lenses of complementary colors. A commercially available presentation program, such as PowerPoint® produced by Microsoft Corporation, is used to create and present the stimuli. As compared to printed material, computer programming has the benefit of presenting in a steady or blinking mode, of specifying the rate of repetition, and the duration of the exposure to the stimulus. For the PowerPoint® program the animation is engaged as follows: (1) highlight the stimulus to be animated, (2) go to Slide Show using the toolbar, (3) select Custom Animation, (4) select Effect, (5) select Flash Once, (6) select Sound and enter the sound file desired, (7) select Order and Timing, (8) select Automatically, (9) select 0.01 seconds or the time desired, (10) select OK. Duplicate the stimulus 6 times or as many times as desired and overlay the images in a stack. Press F5 key to start the animated slide show.

Image 80 in FIG. 7 can be electronically formatted as an example of the computerized embodiment where non-rival and rival stimuli are presented simultaneously. In this example, image 80 is duplicated multiple times and the identical copies are stacked in the identical location, animated, and presented to a subject wearing glasses containing lenses 87 and 88.

Figure 8:
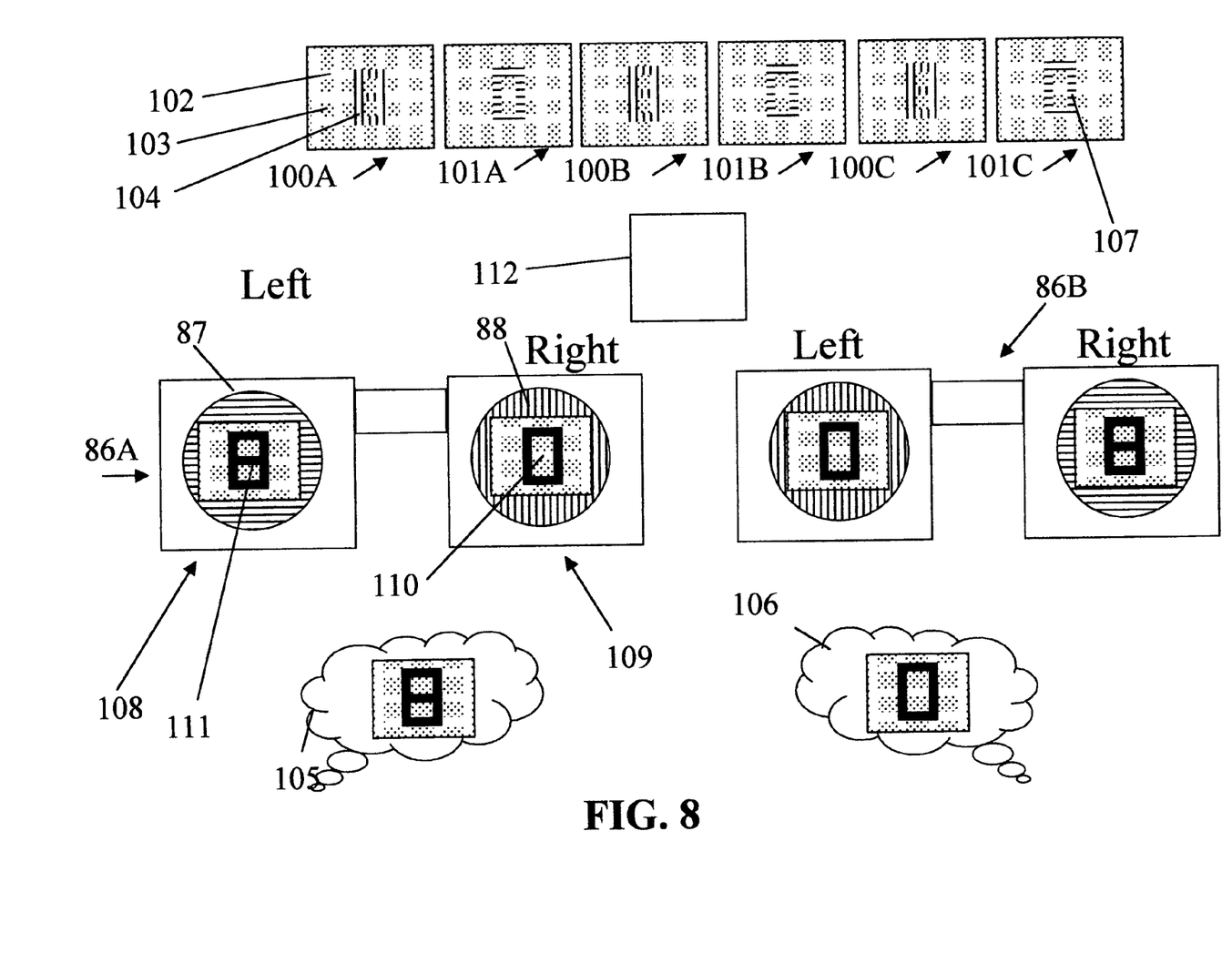
FIG. 8 is a schematic diagram of rival images of complementary colors illustrating a repetitive series.

Another example of the computerized embodiment is illustrated in FIG. 8 where fusible stimuli red 104 (digit 8) and blue 107 (digit 0) form complete recognizable images in complementary colors. After transmittance through red lens 88 and blue lens 87, the rival segments become black line segment 111 and white line segment 110. The fusible non-rival stimuli are the segments forming the shape of digit 0 in images 104 and 107, white lines 102 and gray background 103. Composite images 100A-C and 101A-C appear in the exact same position, position 112, on the monitor and appear alternately in a rapid sequence. With glasses in 86A position, the left eyes sees image 108 or digit 8 and the right eyes sees image 109 or digit 0. Fusion of images 108 and 109 gives percept 105 or digit 8 when the glasses are in the upright position (86A) or the inverted position (86B). Suppression gives percept 106 or digit 0 when the glasses are in one position (position 86B for example) and gives percept 105 or digit 8 when the glasses are in the reverse position (position 86A for example).

Figure 9:
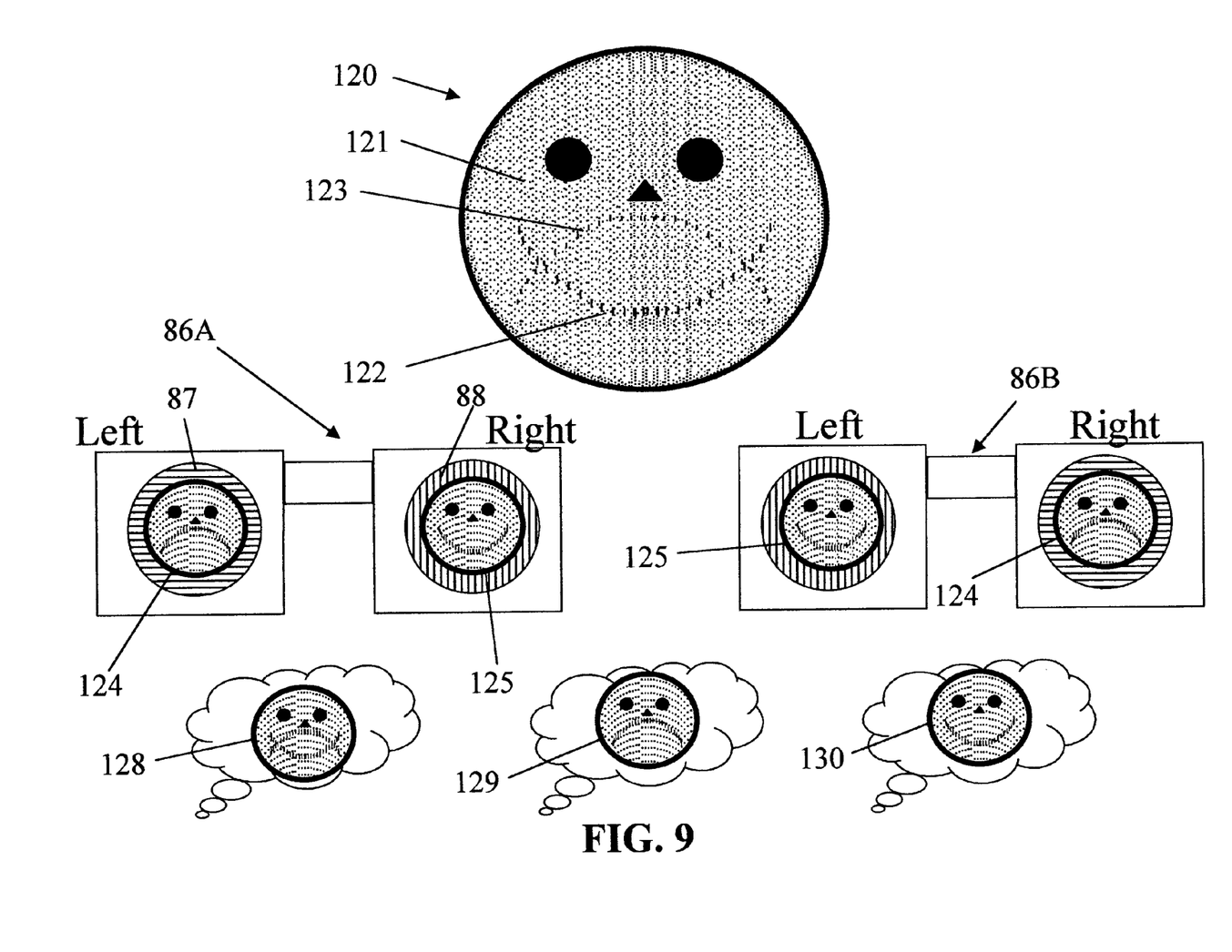
FIG. 9 is a schematic diagram illustrating animated rival features in complementary colors.

Symbols other than digits can be rival stimuli for the computerized embodiment as illustrated in FIG. 9 where different shapes of the mouth alternate the facial expression between "happy face" and "sad face". Stimulus 120 is a face with "happy face" contour 122 in pale blue color and "sad face" contour 123 in pale red color. Contours 122 and 123 are composed of multiple small squares that overlay gray lines 121. When viewing stimulus 120 through blue lens 87, light blue "happy face" contour 122 appears gray and indistinguishable from gray lines 121, while light red "sad face" contour 123 appears dark, and image 120 transforms to "sad face" image 124. When viewing stimulus 120 through red lens 88, light red "sad face" appears gray and indistinguishable from gray lines 121, while light blue "happy face" contour 122 appears dark, and image 120 transforms to "happy face" image 125. Of image 120, only items 122 and 123 are animated. Items 122 and 123 are animated as described above for the PowerPoint® program. Items 122 and 123 are alternated and presented repeatedly in a sequence. The rivalry is between the squares that make up items 122 and 123 and gray lines 121. In the normal sighted person, when observing the presentation through red and blue glasses 86A and 86B, the perception is percept 128 in which the mouth appears to be "talking" as items 122 and 123 appear alternatively and repeatedly. When the weak eye is viewing through red lens 88, "sad face" 129 is perceived and when the weak eye is viewing through blue lens 87, "happy face" 130 is perceived because the opposite healthy eye dominates.

Figure 10:
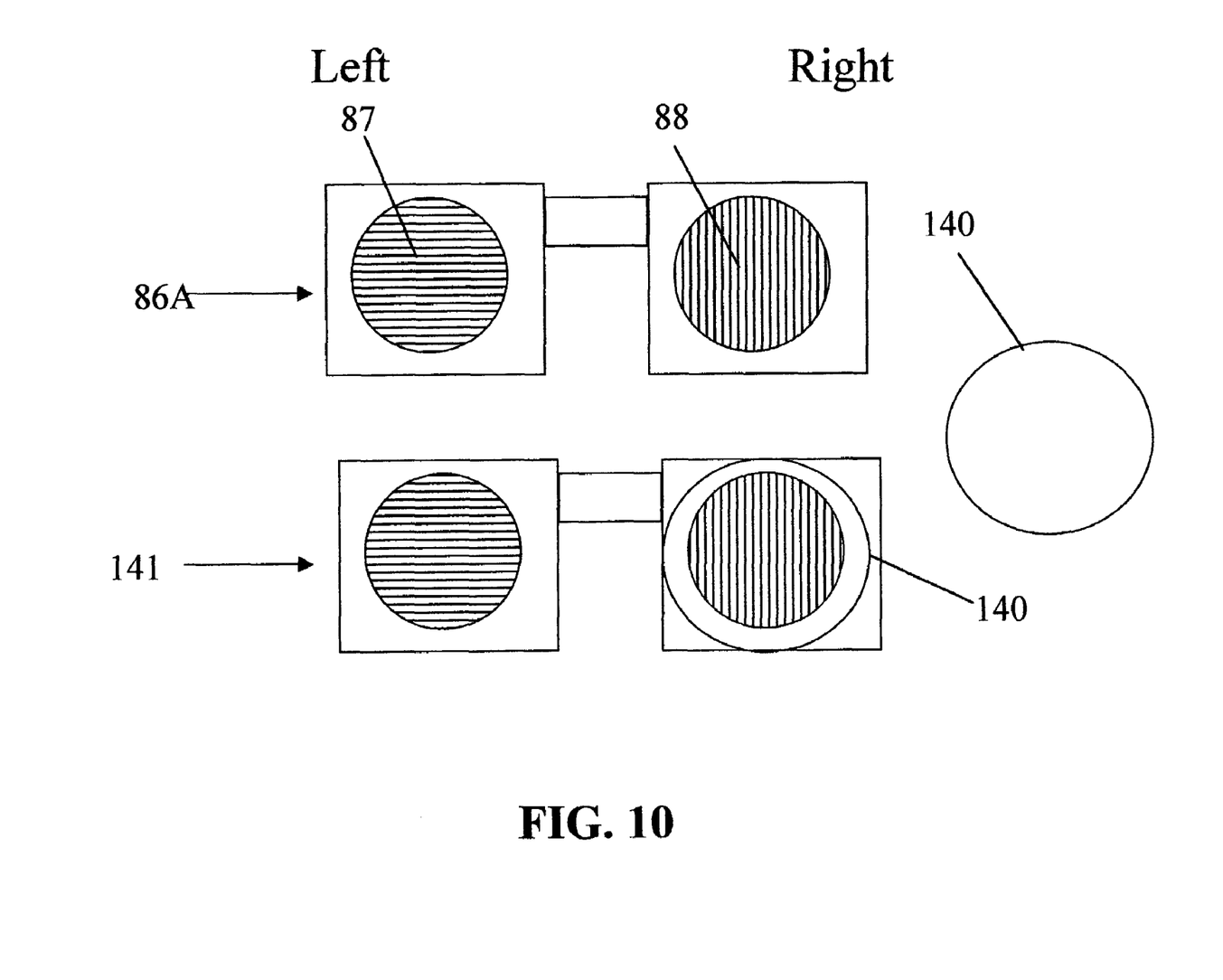
FIG. 10 is a plan view of glasses with lenses of complementary colors and one neutral density filter attached.

In FIG. 10 are red lens 87 and blue lens 88 of the red and blue complementary glasses in position 86A. Attaching neutral density filter 140 over blue lens 88 forms glasses 141. In the normal sighted person there is a tolerance for binocular suppression, that is, the vision to one eye can be dimmed a certain amount before the suppression threshold is reached, the point when one of two rival images occupying the identical visual space is suppressed and the other rival image is perceived. Also in diseases, the weakness can be so small that under rival testing the threshold for suppression is not reached and the weak eye goes undetected. In order to detect small defects with rivalry testing, I have developed red and blue glasses 141 with a filter applied to attenuate the light to one eye. Filter 140 can be applied to either red 88 or blue 87 lens. By using red and blue glasses 141, a small weakness will be amplified and then detectable by rivalry testing. For example, if 1.0 log units interocular brightness difference is physiologically required to suppress one of the rivalry stimuli, a person having a 0.5 log units defect in one eye would be sub-threshold for suppression by 0.5 log units (1.0−0.5=0.5 log units) and perceive the two rival images fused, a normal response. If neutral density filter 140 of 0.9 log units is applied to the weak eye having the 0.5 log units defect, then the interocular difference would be 1.4 log units (0.5+0.9 log units) and above the threshold (1.0 log units) necessary to suppress one of the rival images. However when neutral density filter 140 of 0.9 log units is placed over the normal sighted eye, the interocular difference is only 0.4 log units (0.9−0.5 log units) and below the threshold (1.0 log units) for suppression of one of the rival images. By using the monocular neutral density filter 140 in conjunction with red and blue glasses, a sub-threshold defect has been elevated to a super-threshold defect that allows detection with rivalry testing. Similarly, engaging a neutral density filter in stereoscope 1 and testing in the upright and the inverted positions, sub-threshold afferent defects can be detected.

Operation of Stereoscope

Stereoscope 1 is hand held by the observer. To determine binocularity, the subject is asked to view the images and to tell the number of stars seen (items 46 and 47). When both eyes are viewing, three stars are seen. If only the left eye is viewing, two stars are seen, and if only the right eye is viewing, one star is seen. To determine stereopsis, the subject is told, "From near to far, name the positions of the three object (43A-B, 44A-B, and 45A-B), block, moon, and sun."

To determine vision loss through rivalry testing with stereoscope 1 the procedure is as follows. Lights 8A and 8B in chamber 9 are activated by depressing switch 25A. The film carriage is positioned by sliding lever 5 to the left, which shifts image pair 54A (digit 5) and 54B (digit 2) into the optical pathways. Lever 6A is shifted to the left which positions the 0.9 log units neutral density filter into the pathway of the left eyepiece to create an interocular brightness difference. The filter dims only one of the rival pair of stimuli and does not affect the brightness of items 46, 47, 43A-B, 44A-B, and 45A-B. The subject is instructed, "Watch for a flickering image and tell me what number you see." Switch 25B is depressed which activates timer 24, flasher 23, and lights 21A and 21B. When the cycle is complete, the stereoscope is inverted and the test repeated. If there is no vision loss, digit 8 (item 72) will be seen in both the upright and inverted positions. If digit 5 (item 74) is seen in the upright and digit 2 (item 73) in the inverted position, the defect is in the left eye and if digit 2 (item 73) is seen in the upright and digit 5 (item 74) in the inverted position, the defect is in the right eye. To measure an identified defect, the carriages (items 13B, 13C) holding additional neutral density lenses are shifted in front of the good eye until digit 2 (item 73) changes to a digit 5 (item 74).

Operation of Printed Material and Computerized Imaging

For testing with the printed material or observing images on a screen processed by a computer program, complementary tinted lenses are first positioned with the red lens 88 in front of the right eye and the blue lens 87 with neutral density filter 140 in front of the left eye. The testing is repeated with red lens 88 positioned in front of the left eye and blue lens 87 with the neutral density filter in front of the right eye. A variety of rival image pairs can be present by either printed material or computer program. In FIG. 7 and FIG. 8 digits form the stimuli. The digits perceived will determine if suppression or fusion is the fusional state, and if suppression, the side of the suppression. For example if the stimulus is item 80 of FIG. 7, seeing digit 8 (item 93) with the red and blue glasses 141 in positions 86A and 86B indicates fusion and equality of the two eyes. Seeing digit 9 (item 90) with the red lens over the right eye and digit 6 (item 89) with the red lens over the left eye signifies suppression of the right eye and a defect on that side. Likewise, seeing digit 6 (item 89) with the red lens over the right eye and digit 9 (item 90) with the red lens over the left eye signifies a defect in the left eye.

Turn to FIG. 9. A child is positioned in front of a monitor while viewing through complementary glasses 141 with the red lens before the right eye. The program is activated and the recorded voice announces, "Is the face happy, sad, or talking?" After the child gives a response, the glasses are reversed with the red lens now over the left eye. The program is repeated. A child with a weak right eye sees "sad face" 129 when glasses are in position with the red lens over the right eye and sees "happy face" 130 when the glasses are in position with the red lens over the left eye. A normal sighted child sees the "talking face" 128 when the glasses with lenses of complementary colors are placed in either of the above positions. Abnormal conditions in the illiterate child can be readily detected and the abnormal eye can be identified by this method.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A device for testing binocular vision in humans comprising of:
    (a) an enclosure with right and left eyepieces and focusing lenses,
    (b) a front chamber and a rear chamber with each chamber having independent lighting,
    (c) a backdrop in said front chamber for mounting stereograms, fusible images, and non-fusible images that are viewable through the eyepieces,
    (d) a two-way mirror partitioning said front chamber from said rear chamber that separates said backdrop in said front chamber from a rival image pair consisting of a right rival image and a left rival image located in said rear chamber so that said rival image pair is illuminated primarily from light from said rear chamber and said rival image pair is visible through said evepieces only when the illumination is brighter in said rear chamber than in said front chamber,
    (e) means of providing sufficient energy to illuminate said front and rear chambers,
    (f) means of independently switching on and off the lighting of said front chamber and said rear chamber,
whereby, images can be viewed by children and adults for measurement of binocularity, stereopsis, and binocular rivalry concurrently, or binocular rivalry can be measured separately from binocularity and stereopsis.

2. A device according to claim 1 having means of providing light brightness attenuation selectively to said right or left rival images.

3. A device according to claim 1 having two adjustable eyepieces housing focusing lenses that move horizontally to accommodate subjects having different interpupillary distances.

4. A device according to claim 1 where the device is hand-held and the images presented to the right and left eyes can be reversed as to the right and left sides by inverting said device causing said right rival image to be viewed by the left eye and said left rival image to be viewed by the right eye.

5. A device according to claim 1 where the illumination of said rear chamber is flashing and the flashing is adjustable as to the duration of the flash and the interval between flashes.

6. A process of formatting visual stimuli consisting of:
    (a) presenting similarly shaped non-rivalrous fusible stimuli of similar binocular luminance and
    (b) presenting similarly shaped rivalrous fusible stimuli of different binocular luminance,
whereby, binocularly viewed stimuli form distinctive identifiable shapes that transform during perception and distinguish fusion from suppression.

7. A process according to claim 6 where said non-rivalrous and rivalrous stimuli are composed of complementary colors, viewed through lenses of said complementary colors, and presented on printed material.

8. A process according to claim 6 where said non-rivalrous and rivalrous stimuli are composed of complementary colors, viewed through lenses of said complementary colors, and presenting simultaneously or sequentially by a computer program for viewing on a monitor.

9. A process according to claim 6 where said non-rivalrous and rivalrous stimuli are composed of complementary colors, viewed through lenses of said complementary colors, and presenting simultaneously or sequentially by a computer program for viewing on a projection screen.

10. A process according to claim 6 where said non-rivalrous and rivalrous stimuli are composed of complementary colors, presenting simultaneously or sequentially in a computer program for transmission over the Internet, and viewing on a monitor through lenses of said complementary colors.

11. A process according to claim 6 where said non-rivalrous and rivalrous stimuli are viewed through a stereoscope.

12. A device consisting of a pair of eyeglasses having a right lens and a left lens of complementary colors with means of attenuating the brightness of the light passing through one or both of said lenses to cause an interocular brightness difference.

13. A device according to claim 12 in which said eyeglasses are functional when the right and left sides are reversed so that said right lens is in front of the left eye and said left lens is in front of the right eye.

* * * * *